US010792456B2

(12) United States Patent
Wolfram et al.

(10) Patent No.: US 10,792,456 B2
(45) Date of Patent: Oct. 6, 2020

(54) ARRANGEMENT AND METHOD FOR THE IN-VITRO AND IN-VIVO TREATMENT OF BRONCHIAL TUMORS

(71) Applicant: SRH Wald-Klinikum Gera gGmbH, Gera (DE)

(72) Inventors: Frank Wolfram, Jena (DE); Thomas Lesser, Gera (DE)

(73) Assignee: SRH Wald-Klinikum Gera gGmbH, Gera (DE)

(*) Notice: Subject to any disclaimer, the term of this patent is extended or adjusted under 35 U.S.C. 154(b) by 1302 days.

(21) Appl. No.: 14/904,906

(22) PCT Filed: Jul. 9, 2014

(86) PCT No.: PCT/DE2014/000368
§ 371 (c)(1),
(2) Date: Jan. 13, 2016

(87) PCT Pub. No.: WO2015/007264
PCT Pub. Date: Jan. 22, 2015

(65) Prior Publication Data
US 2016/0144147 A1    May 26, 2016

(30) Foreign Application Priority Data
Jul. 15, 2013    (DE) .................. 10 2013 011 964

(51) Int. Cl.
*A61M 16/14*    (2006.01)
*A61N 7/02*    (2006.01)
(Continued)

(52) U.S. Cl.
CPC ......... *A61M 16/147* (2014.02); *A01N 1/0236* (2013.01); *A61M 16/0404* (2014.02); *A61N 7/02* (2013.01); *A61B 2018/00541* (2013.01); *A61B 2018/00577* (2013.01); *A61B 2018/00791* (2013.01); *A61B 2090/374* (2016.02);
(Continued)

(58) Field of Classification Search
CPC ........ A61N 5/1048; A61N 7/02; A61N 7/022; A61N 2007/0043; A61N 2007/0052–0091; A61N 2007/025–0027; A61M 16/00; A61M 16/20–209;
(Continued)

(56) References Cited

U.S. PATENT DOCUMENTS 5,158,536 A * 10/1992 Sekins .................... A61F 7/123
604/20
6,409,720 B1 * 6/2002 Hissong ................. A61N 7/022
128/898
(Continued)

FOREIGN PATENT DOCUMENTS

| WO | WO-91/03267 | 3/1991 |
| WO | WO-02/096504 | 12/2002 |
| WO | WO-2004/075977 | 9/2004 |

*Primary Examiner* — Samchuan C Yao
*Assistant Examiner* — Ned T Heffner
(74) *Attorney, Agent, or Firm* — Norris McLaughlin, P.A.

(57) ABSTRACT

Lung tumors are treated in-vitro and in-vivo by an apparatus and method for operating the apparatus wherein the lung being treated is made receptive to ultrasound in order to allow the ultrasound waves to be guided through the healthy lung tissue to the tumor tissue in an optimized manner for the use of FUS therapy.

6 Claims, 11 Drawing Sheets

(51) Int. Cl.
    *A61M 16/04*     (2006.01)
    *A01N 1/02*     (2006.01)
    *A61B 18/00*     (2006.01)
    *A61N 7/00*     (2006.01)
    *A61M 16/10*     (2006.01)
    *A61B 90/00*     (2016.01)

(52) U.S. Cl.
    CPC ... *A61B 2090/376* (2016.02); *A61B 2090/378* (2016.02); *A61B 2217/007* (2013.01); *A61M 16/109* (2014.02); *A61M 2202/0208* (2013.01); *A61M 2202/0468* (2013.01); *A61M 2205/058* (2013.01); *A61M 2205/33* (2013.01); *A61M 2205/3368* (2013.01); *A61N 2007/0004* (2013.01); *A61N 2007/0082* (2013.01); *A61N 2007/0086* (2013.01); *A61N 2007/027* (2013.01)

(58) Field of Classification Search
    CPC ..... A61M 16/0003–0012; A61M 16/06–0694; A61M 2016/0015–0042
    See application file for complete search history.

(56) References Cited

U.S. PATENT DOCUMENTS

2004/0039280 A1*   2/2004   Wu ................... G01R 33/4804
                                                              600/412
2008/0247506 A1*  10/2008   Maschke ................ A61B 6/12
                                                              378/15

* cited by examiner

ARRANGEMENT AND METHOD FOR THE IN-VITRO AND IN-VIVO TREATMENT OF BRONCHIAL TUMORS

BACKGROUND OF THE INVENTION

The invention relates to an apparatus for the treatment of lung tumors outside or in the human body and a method for the treatment of lung tumors outside the human body.

According to the Cancer Registry it is known that most common primary tumors are tumors of the lung, breast, prostate and bowel. The lung, moreover, represents the first filtration location for all primary tumors situated in the flow of the vena cava, which preferably leads to metastases.

Surgical procedures of lobectomy or pulmonary metastases resection are in the main the only methods available for the curative therapy of malignant lung processes, in particular of metastases. However, these methods require a functional operability of the lungs, are associated with loss of parenchyma and are no longer applicable in most relapses.

For the therapy of pulmonary metastases, thermal methods are known, too. In radiofrequency ablation, for example, a microwave probe is used to pierce through the thorax and pulmonary tissue into the metastasis. This probe emits microwaves that are converted into heat by the surrounding tumor tissue. Recent studies show that in 5 to 10% of cases this method leads to serious complications, such as pneumothorax or hemothorax. In addition, this therapy is not radical, i.e. not comprehensive enough, so that it frequently happens that tumor cells are not reached which leads to a relapse. Therefore, this method is only used in palliative medicine.

High-intensity focused ultrasound (FUS, HIFU) is a medical application of ultrasound in which the tissue is indirectly or directly heated by the absorption of sound waves. This therapeutic procedure is also called ultrasound ablation, generally focused ultrasound surgery (FUS), and is currently used for the treatment of prostate cancer by some urological centers around the world, but in principle it is also known for the treatment of liver, breast and thyroid cancer.

Pulmonary tissue in ventilated condition is an impenetrable barrier for ultrasound due to the reflection at the gas-liquid-interface. Therefore, the substitution of the gas component by an ultrasound-conductive liquid is required.

The flooding of a part of the lung or of the entire left or right lung is basically known from the publication by Lesser et al. "*Lung flooding—a new method for complete lung sonography*. Res. Exp. Med., 1998, Vol. 198, pp. 83-91. In the procedure described, pure oxygen is ventilated by respiration in the part to be flooded for at least 20 minutes. Subsequently, a physiological saline solution is introduced into the part of the lung to be flooded. The residual air in the lung alveoli is absorbed via the bloodstream and a gas-free liquid-pulmonary-tissue mixture remains, which can be treated by sonography.

This method is only used for diagnostic purposes under video-assisted thoracotomy (VATS) (see publication by Klinzing S., Lesser Th., Schubert H., Bartel M. and Klein U. "*One lung flooding for video-assisted thoracoscopic surgery in animal experiments on pigs*." Resp Exp Med, 2000, Vol. 199, pp. 333-337) so that the surgical measure can be supported intraoperatively by ultrasound imaging.

In this method, the lung can be flooded successfully and free of gas. The disadvantage, however, is that the procedure is very time-consuming and requires a flooding time of about 30 minutes, in which damage to healthy pulmonary tissue can already be caused since under flooding the blood supply of healthy parenchyma is suppressed (so-called ischemia).

Although the time period required for the complete gas-free flooding is reduced by a reduction of the gas (oxygen) volume contained in the lung achieved by suction (P−: 0 to 20 cm $H_2O$) before flooding, and during the flooding process an overpressure of about 5 cm to 20 cm $H_2O$ can be applied to the part of the lung which is not to be flooded and further ventilated to maintain the oxygenation, but the procedure described in the publication cited is only useful for ultrasound diagnostics due to the short flooding periods to be kept and the residual gas rates associated with these short flooding periods.

From the publication WO2002/096504 A2 the therapy of lung cancer by ultrasound is known in principle. In this treatment, an ultrasonic transducer is inserted into the lung bronchus (i.e. endrobronchially supported) or is used to directly pierce into it from the outside (i.e. supported interstitially) so that a direct contact is established between the ultrasonic transducer and the tumor.

The disadvantage of this solution is that due to the invasive nature of the therapy the thoracic cavity and the lung parenchyma are injured; the therapy is carried out in ventilated, normally respirated lung tissue. This type of treatment often leads to post-operative complications, such as pneumothorax.

The WO2004/075977 A2 describes a therapy of lung cancer by diffuse ultrasound coupling (hyperthermia). For this treatment, it is necessary that the lung tumor, due to its growth, reaches the chest wall and pleura or starts from there. If this condition is met, the ultrasound of an extra-costally mounted sound transducer can reach the lung tumor through the chest wall and pleura as long as there is no aerated pulmonary tissue between the tumor cells and the sound transducer.

The disadvantage of this therapy performed in ventilated lung condition is that there must be no aerated lung tissue between the tumor cells and the sound transducer and that the therapy is designed as radio hyperthermia, i.e. the heating is induced by ultrasound and ionizing radiation is applied.

The publication U.S. Pat. No. 5,158,536 describes an apparatus and a method for the therapeutic treatment of lung tumors, in which a part of the upper bronchial branch (birfurcation) is separated from the residual pulmonary system by means of a closing element in order to introduce subsequently a highly ultrasound-absorbing liquid (PFC) into said system, whereby an ultrasonic transducer is placed intrabronchially into this liquid. The energies of the ultrasonic transducer are absorbed by the liquid, which is heated through this absorption. If the bronchial branch, which is filled in this way and provided with ultrasound, is directly infiltrated by a tumor or if the tumor is located directly adjacent to the bronchial wall, the thermal energy of the ultrasound-absorbing liquid will be directly transmitted to it; however, this procedure does not allow flooding of the peripheral parenchyma.

According to the disclosure of U.S. Pat. No. 5,158,536, sound transducers can also be applied to the thorax wall by putting the ultrasound probe outside the body of the patient to be treated, namely, onto the ribs of the patient to heat up the ultrasound-absorbing liquid intrabronchially.

This technical solution has the disadvantage that it is the ultrasound-absorbing liquid and not the tissue to be treated that is directly heated in order to treat the lung tumor (to ablate it).

In addition, the gas volume is removed from the bronchial branch by lavage. In this process, a continuous flow of the liquid is introduced into the upper bronchial branch and sucked out again. Gas is indeed flushed out but this flushing out is not free of residual gas and the gas components lead to a less effective heating, because in contrast to the ultrasound-absorbing liquid the gas does not absorb ultrasound.

The flushing out procedure also has the disadvantage that the surfactants of the surfaces in the lung are also flushed out, which can lead to postoperative respiratory failure.

According to U.S. Pat. No. 5,158,536, the flooding is performed by continuously filling the lung without several filling or discharging steps, and the therapy requires direct infiltration into the bronchial structure of the lung to be able to establish mechanical conductivity with the sound transducer. Since the majority of tumors are centrally surrounded by the ventilated (gas-containing) lung parenchyma, the method described cannot be applied to these tumors because the parenchyma tissue is a high-grade sound isolator/reflector.

The above-mentioned lung cancer therapy solutions by means of ultrasound have the disadvantage that the tumor has to be in direct contact with the sound transducer, be it at a bronchus, at the chest wall or the pleura. Most lung tumors, however, are not at these locations but are situated centrally, surrounded by healthy and ventilated tissue, which makes it impossible to focus the ultrasound in the lung tumor cell tissue.

SUMMARY OF THE INVENTION

Therefore, the object of the invention is to avoid the disadvantages of the prior art described above and to provide an apparatus and a method for operating this apparatus, which makes the lung sound-receptive for the application of the FUS therapy in order to be able to guide the mechanical ultrasonic waves optimally through the healthy pulmonary tissue to the tumor tissue.

The aim of the invention is to heat the tumor tissue completely and exclusively through the thermal effect of ultrasound and thus to destroy it. In this process, thermal heating of 20 K is required so that a temperature of >55° C. is reached within the entire tumor volume.

According to the invention, this task is fulfilled by providing an apparatus and a method for heating lung cancer cell areas with the aid of ultrasound under lung flooding.

The nature of the invention is to provide an apparatus which allows an optimum ultrasound ablation (FSU therapy) by means of a specific combination of lung flooding (with a liquid, preferably physiological saline solution) and the application of focused therapeutic ultrasound waves in lung cancer cell areas/in the areas of the lung metastases.

The apparatus for in-vitro and in-vivo treatment of lung tumors comprises at least one ventilation and respirator system for supplying gas to the part of the lung that is to be ventilated and flooded, a device for flooding a part of the lung with physiologically compatible liquids, a therapy system with at least one therapeutic ultrasonic transducer, an imaging-monitoring system and a temperature-monitoring system, as well as a central control unit.

In such an apparatus, the central control unit has a data transfer connection to a unit which operates and controls the therapeutic ultrasonic transducer (position and performance of the ultrasound), to the ventilation system, to the apparatus for the targeted ventilation and flooding, to the imaging-monitoring system and to the temperature-monitoring system.

The respirator system and the apparatus for the controlled ventilation and flooding have a gas- and liquid-conducting connection to a system of tubes (preferably double-lumen tube) (one tube of the ventilated part of the lung is gas-conductive and one tube of the part of the lung to be flooded is gas- and liquid-conductive) so that the gas is conducted through one tube and the liquid is conducted through the other tube, whereby the double-lumen tube can be inserted in an intratracheal manner into a lung which contains a lung tumor.

In the operating mode of the apparatus, ultrasonic therapeutic doses can be dispensed from the ultrasonic transducer, and these ultrasonic doses can be guided in a controlled manner through the flooded part of the lung to the tumor tissue contained (in a tumor-containing lung outside or inside a human body) to treat the lung tumor.

In order to flood the lung or parts of the lung, the apparatus is provided with control elements, which regulate the gas and liquid flows and lead oxygen, negative pressure and a liquid, preferably a physiological saline solution, together to a common supply line (e.g. a controllable three-way valve) which can be connected with the part of the lung that contains the lung cancer to be treated, such that the part of the lung connected to the apparatus is separated in a gas- and liquid-tight manner from the rest of the lung, which is ventilated by a conventional ventilator.

The supply line opens into a lung tube, via which the gas or liquid can be supplied to or taken from the part of the lung, which includes the lung cancer to be treated.

After completion of the oxygen ventilation, a physiological saline solution can be supplied via the lung tube to the part of the lung to be treated.

After successful flooding of the part of the lung which contains the cancer to be treated, an acoustic contact of an ultrasonic transducer (power ultrasonic transmitter) is established by means of the supplied saline solution with the lung cancer tissue via the healthy lung tissue subjected to the ultrasound, whereby this contact can be focused so that ultrasonic doses can be bundled unhindered and directed in a controlled manner to a predetermined area in the tumor volume.

The lung flooding with physiological saline solution ensures that gas-containing tissue, which is a high-degree reflector for acoustic waves, is no longer present in the flooded part of the lung, so that an optimum ultrasound ablation by means of focused therapeutic ultrasonic waves is possible in-vitro and in-vivo, whereby only the heat energy is used for tumor destruction.

It is also part of the invention to use the lung flooding with physiological saline solution for the extracostal biopsy or for the insertion of an agent into the tumor while the lung is partially flooded.

This feature offers the advantage that centrally located tumors and metastases can be represented and punctured very well by imaging ultrasound. The imaging system makes it possible to insert a biopsy needle to take tissue sample or inject with use of a syringe one or several agent(s) into the lung tumor in a controlled manner. This can be done extracostally or intracostally from the flooded bronchial system. In this way, it is possible to take a tissue sample within a few minutes and then the sample is examined outside the human body in order to make a pathological diagnosis. During said period, the flooding of the lung can be maintained.

The result of the pathological diagnosis makes it possible to set exact parameters for the controlled heating of the lung tumor tissue within the flooded lung by therapeutic ultrasound.

The invention will be further explained by means of the schematic drawings. They show:

FIG. 1a: a general survey representation of the inventive apparatus,

FIG. 1b: an overview representation for using the apparatus according to FIG. 1 in the human body, FIG. 2: an overview representation for using the apparatus according to FIG. 1 on a part of the lung outside the human body, FIG. 3a: a schematic representation of the ultrasonic transducer according to FIG. 1 in a position outside the human body, FIG. 3b: a schematic representation of the ultrasonic transducer according to FIG. 1 in a position inside the human body after the surgical opening of the thorax and pleura, FIG. 3c: a schematic representation of the ultrasonic transducer according to FIG. 1 in a position inside the human body above the diaphragm after the surgical opening of the abdominal area, FIG. 3d: a schematic representation of the ultrasonic transducer according to FIG. 1 in a position inside the human body between coastal pleura and intercostal area by means of a surgical intervention, FIG. 4: a schematic representation of the control of the inventive apparatus used according to FIG. 1b, FIG. 5: a schematic representation of the control of the inventive apparatus used according to FIG. 1b, FIG. 2 or FIG. 3a through d, FIG. 6: a representation of the control process during the flooding of the lung, and FIG. 7: a representation of the control process during the deflooding of the lung.

The apparatus shown in FIG. 1a for lung flooding with image-based control of a therapeutic ultrasonic transducer includes a ventilation and respirator system (1) for the part of the lung to be respirated, an apparatus for the targeted ventilation and flooding (2) of a part of the lung with liquid, a system for therapeutic purposes (4) and a central control unit (5).

The ventilation and respirator system (1) and the system for the controlled ventilation and flooding of a part of the lung with liquid (2) are combined by tubes, which can be inserted intratracheally.

In this method, a double-lumen tube (3) is used for flooding a lung or, in the case of a pulmonary lobe, an endobronchial blocker is also employed.

The therapy system comprises at least one therapeutic ultrasonic transducer (40), an imaging-monitoring system (42) and a temperature-monitoring system (41).

All functional elements for the control of the pressures and volume flows of gases and liquids and of the position of the ultrasonic transducer and its performance are controlled by the central control unit (5). It receives the necessary information about the location of the tumor from the imaging-monitoring system (42). The temperature in the lung tumor is recorded by the temperature-monitoring system (41). All data collected will be transferred to the control unit (5) via data transfer cables.

The apparatus for the controlled ventilation and flooding (2) of a lung or of part of the lung with liquid consists of at least three units, which are able to deliver liquid and gas, pressure or volume in a controlled manner from a connected reservoir (12; 20; 22).

Each unit has a connection with a negative pressure, i.e. vacuum or underpressure (20), a gas connection for pure oxygen (12) and a connection for a physiologically compatible liquid brought to the right temperature (22). The liquid is preferably provided at the connection from a reservoir, which is set to a predetermined temperature by a control element (25) in a heating reservoir (24). From this apparatus, a connecting element (9) leads to the tube, which separates the part of the lung to be flooded from the ventilated part.

The individual controlled gas and liquid flows are led by a controlled three-way valve (13) into a lung tube (3) via a port (8) and a port (9). This process is carried out by the control unit (5), but principally it can also be done manually.

The part of the lung to be ventilated is supplied by the ventilation and respirator system via the tube or lumen (30) of the DLT (double lumen endobronchial tube) via port (8). Generally, this function can also be carried out by a commercial respirator system. This ventilation and respirator system (1) has at least one setting device (10) for pressure and/or volume control of a connected air supply (11) and/or oxygen supply (12). The individual pressure or volume ratios are led via a three-way valve (13) or via a manual connection to the connecting element (8) and to the part of the lung to be ventilated at the lung tube (30).

Optionally, the ventilation and respirator system (1) can supply both lung areas for the period of a joint ventilation, thus in the oxygen enrichment phase (T1-T2) or after deflooding (T3-T4). For this purpose, the two lung tubes (30; 31) are put together.

The lung tube (3) consists of at least two tubes (30; 31), designed for example as hose or pipe elements, and at the trachea they can be separated from the atmospheric ambient air by at least one block (32). The lung area to be flooded is separated from the ventilated area by at least one further block (32'). This is done for a lung in the bifurcation of the bronchial branch by a double lumen tube and for a lung lobe in the bronchial area (i.e., bronchi or lower trachea) by an endobronchial blocker.

The central functional element of the therapy of a tumor-containing flooded lung outside or inside the human body is at least one ultrasonic transducer (40) which can bundle its therapeutic doses in at least one therapeutic area (46).

This ultrasonic transducer (40) is preferably designed as a focusing sound transducer; whereby the focusing can be achieved by a spherical geometry or a phase-shifted excitation of individual elements on a transducer surface.

To ideally guide the therapeutic area (46) of the ultrasonic transducer (40) into the tumor volume it is helpful if the transducer can carry out position shifts in space and tilting movements around its own spatial axes. This movement is centrally predetermined by the control unit (5) and realized by a motor unit (45) mounted on the ultrasonic transducer (40).

If in addition, the focal position due to the beam forming is changed by the phase-shifted actuation of the single elements of the ultrasonic transducer (40), e.g. in distal direction from the transducer surface, this change will be performed by a beam-forming unit (44) which can also change the performance of the ultrasonic transducer (40) and thus the size of the focal therapeutic area (46).

The information about the position of the tumor in the flooded lung tissue of a lung located outside or inside a human body is required for the control of the therapeutic area (46). This position information is provided by the imaging-monitoring system (42), which is conveniently based on ultrasound imaging, for example in B-mode typical in medicine.

However, according to the invention, methods based on MRT or CT technology are also applied.

If an ultrasound imaging technique is used, it is useful for design reasons to integrate the imaging and the therapeutic elements into the ultrasonic transducer (40).

The image information of the tumor tissue-containing lung flooded with liquid is transmitted to the central control unit (5) in which the spatial anatomic conditions and the position of the therapeutic area (46) are analyzed and combined in a coordinate system.

On this basis, a planning algorithm is determined which optimizes the control of the ultrasonic transducer (40) via its movement and beam-forming degrees of freedom. It is important that the therapeutic area (46) of the ultrasonic transducer (40) can reach the entire tumor volume (35).

Since the energy deposition of the ultrasonic transducer (40) in the tumor volume undergoes fluctuations on the way to the target area due to scattering losses and inhomogeneities, it is generally recommended to monitor the temperature by means of the temperature-monitoring system (41), which can be designed in the simplest case as a thermocouple element which is invasively inserted through the flooded lung tissue. A measuring converter (43) converts the physical measurand of the temperature-monitoring system (41) in a suitable data format to be further processed in a central control unit (5).

However, since a non-invasive method is to be preferred for medical reasons, MRT (magnetic resonance tomography) or ultrasound is preferably used as a temperature-monitoring system (41) [and simultaneously as an imaging-monitoring system (42)]. In this way, one single measurement technique can be applied as an imaging and thermally sensitive method.

The apparatus shown in FIG. 1b for lung flooding in humans with image-based control by a therapeutic ultrasonic transducer (40) for the therapy of lung tumor (35) in the flooded part of the lung (34) comprises a ventilation and respirator system (1) for the part of the lung to be respirated (33) as well as a system for ventilating and flooding (2) the remaining part of the lung (34) with liquid.

These two systems are connected by means of a lung tube (3) with a first lung tube lumen (30), a second lung tube lumen (31) and a block (32). Here, the lung tube (3) is tracheally inserted into a patient so that the tubes or lumens (30; 31) are separated from the atmospheric gas space by at least one block (32).

The supply from the ventilation and respirator system (1) is realized via a line (8).

The second lung tube (31) separates the part of the lung to be ventilated and then flooded from the part of the lung to be ventilated by means of one or several block(s). Now, the part of the lung to be flooded, which has been saturated with oxygen, can be ventilated under increasing pressure and filled via a line (9) from the device for the controlled ventilation and flooding (2), whereas the respirated part of the lung (33), which is required for maintaining oxygenation, is supplied by a respirator system (1).

The subsequent procedure corresponds to the illustration in FIG. 1a.

In this procedure, the therapeutic area (46) of the ultrasonic transducer (40) is aimed at the lung tumor (35) which is located in the flooded part of the lung (34). This can be achieved via the intercostal space (37) by means of a suitable configuration of the ultrasonic transducer (40) (see FIG. 3a). Further application embodiments are explained in the descriptions for FIG. 3b-d.

Thanks to its spatial mobility, the ultrasonic transducer (40) can reach the volume of the lung tumor (35) or a part thereof so that the sound intensity of the ultrasonic transducer (40) is absorbed by the lung tumor volume and simultaneously heats it up. This process is called ablation if this heating reaches thermal doses which lead to the destruction of tumor cells. According to the invention, a target temperature of >55° C. is reached in the lung tumor (35) surrounded by the flooded lung tissue.

It is implicit in the present invention that ventilation must be resumed after the ultrasonic treatment (and surgical reattachment of the lung to veins and arteries in the case of in-vitro treatment) in order that the lung functions sufficiently during healing, and the liquid, which perfuses the lung, is resorbed into the patient's body.

FIG. 2 shows the schematic design for the HIFU therapy of a lung tumor (35), which is surrounded by flooded lung tissue, and this therapy is performed outside the human body after the operative removal of the lung.

In this procedure, one lung (34) or a part thereof containing one or several lung tumor(s) (35) is flooded as described above and thus can be removed in a flooded condition by a surgical measure comparable to a lung transplantation. Subsequently, the ultrasound therapy is performed outside the body.

After the successful treatment of at least one lung tumor (35), this part of the lung is surgically reimplanted into the body within a short period of time, and the bronchial structure and vessels are reconnected.

The apparatus for treatment outside the human body comprises a device for the controlled gas ventilation and flooding (2) of the lung with a liquid, one or several ultrasonic transducer(s) (40), the position of which is changeable, a temperature-monitoring system (41) and an imaging-monitoring system (42) for monitoring the lung tumor (35) in the flooded part of the lung (34), and both systems transfer the temperature and localization data of the lung tumor (35) in the flooded pulmonary lobe to a central control unit (5).

To keep the liquid in the flooded part of the lung (34), the central access of the bronchial branch must be sealed either through the device for maintaining the flood underpressure using at least one block (32) or, in the simplest case, said access must be disconnected in the area of the bronchial branch (51) after flooding.

As previously described in detail for FIGS. 1a and 1b, the flooding is carried out directly at the lung of a patient. Afterwards, the flooded lung part can be removed, whereby the bronchial branch connected to the rest of the lung tissue must be severed.

Furthermore, the lung must be disconnected from the venous and arterial blood vessels (36) and sealed temporarily. The lung, which can now be easily removed, is delivered to the therapy system. A suitable coupling of the lung for the ultrasound can be prepared, in the simplest manner, by means of a supply of physiological saline solution, like a bath. The therapy is carried out as described above for FIGS. 1a, 1b and 5.

An advantage of this form of application outside the human body is the unrestricted access of the therapeutic sound because the lung is acoustically accessible from all sides. This is particularly advantageous in the case of multiple or large lung tumors. However, this approach is highly invasive.

FIG. 3a shows a schematic drawing of the application of the ultrasonic transducer (40) for the therapy of a lung tumor (5) in a flooded part of the lung, wherein the transducer (40) is applied extracostally, i.e. outside the human body.

This is a non-invasive application of at least one ultrasonic transducer (40) for introducing therapeutic ultrasound into a lung tumor (35) which is surrounded by flooded lung tissue (34). In this procedure, the ultrasonic transducer (40) is directly applied to the intercostal muscles of the intercostal space (37) or it is applied with a specific distance to the thorax such that the impact area of the ultrasonic transducer (40) is located within the lung tumor (35).

If the ultrasonic transducer (40) has a distance to the thorax due to structural reasons, a well-conducting ultrasound coupling medium (47) must be provided between the thorax wall (37) and the ultrasonic transducer (40) in an air-barrier-free manner.

The energy of the ultrasonic transducer (40) must not impact on the ribs (38) because this impact can cause local heating and hence damage to normal tissue as well as complications. This means that the ultrasonic transducer (40) is controlled constructive-mechanically and/or by phase-shifted actuation of its individual elements (beam forming) in such a manner that the ultrasonic energy is led through the ribs (38), via the rib muscles, to the lung tumor (35).

The advantage of this approach is the minimal invasiveness such that the thoracic cavity is not opened. The disadvantage, however, is the restricted accessibility of the tumor volume depending on the anatomy of the ribs and the lung tumor location. In addition, the applied ultrasonic energy loses intensity by absorption when passing the rib muscles, and this intensity is then lacking in the operational area. If the patient is very obese, the loss can lead to problems. This kind of application is especially suitable for the therapy of lung tumors after filling the lower lobe of the lungs with liquid because here the distances between ribs (38) are the largest ones for anatomical reasons.

FIG. 3b shows the schematic view of the application of an ultrasonic transducer (40) for the therapy of a lung tumor (35) in a flooded part of the lung (34), whereby the thorax and the pleura (39) have been opened in a surgical intervention and the ultrasonic transducer (40) has been applied to the flooded lung (34).

For different therapeutic measures, the thoracic cavity must be opened by a so-called thoracotomy (THT). This step does not necessarily have to be associated directly with the therapeutic measure and can also be done for diagnostic purposes. According to surgical guidelines, the lymph nodes of the thoracic cavity must be removed and subject to pathological examination if the tumor identity is not known and tumor spreading is assumed. In addition, the space between two ribs (38) is widened by means of the surgical intervention so that a large window is generated for inserting an ultrasound transducer (40).

Here, the ultrasonic transducer (40), which preferably contains diagnostic and therapeutic elements, is positioned directly on the surface of the flooded part of the lung (34) or placed on it by a suitable coupling medium (47).

The therapeutic area of the ultrasonic transducer (40) can be guided through the tumor volume (35) by manual or mechanical-electrical control.

A great advantage of this kind of use of the ultrasonic transducer (40) is its good access to the surface of the flooded part of the lung so that it can be placed in an ideal position for therapeutic purposes. If moreover, multiple tumors exist in the lung, this kind of application is to be preferred, although due to the location and anatomy of the tumors it cannot be guaranteed by extracostal application (s. FIG. 3a) that all of them can be treated.

FIG. 3c represents the schematic view of the application of the ultrasonic transducer (40) via the diaphragm (50) for the therapy of a lung tumor (35) in a flooded part of the lung (34) after the surgical opening of the abdominal cavity.

This form of application offers a good acoustic coupling of the ultrasonic transducer (40) without the opening of the thoracic cavity.

This application prevents infections and the entry of air, which can lead to complications and a collapse (pneumothorax) of the lung, which must then be provided with a drainage.

Since the abdominal cavity can easily be opened by opening the abdominal wall, an ultrasonic transducer (40) can be placed at the underside of the diaphragm (50) by appropriate guidance and positioning.

The ultrasonic transducer (40) has a suitable acoustic window for coupling therapeutic ultrasound in the flooded lung (34) via the diaphragm (50) and pleura (39), which is not an acoustic barrier.

In addition, the diaphragm (50), if located below a flooded lung (34), is very elastic so that the ultrasonic transducer (40) can be very well adapted to the shape of the diaphragm (50), which does not represent an acoustic barrier, and it thus represents an ideal means of coupling to the flooded lung (34) containing the lung tumor (35).

The therapeutic area of the ultrasonic transducer (40) can be guided over the volume of the lung tumor (35) by an appropriate, manually or mechanical-electrically controlled movement of the ultrasound transducer (40).

The diaphragm (50) has a large surface so that the therapy of preferably large or multiple foci in the lower part of the flooded lung (34) is possible, and invasiveness is kept within limits.

FIG. 3d shows the schematic view of an endoscopic application of the ultrasound therapy of a lung tumor (35) in a flooded part of the lung, and in this application the ultrasonic transducer (40) has been positioned between pleura (39) and intercostal space (37, 38). The ultrasound can be introduced directly into the flooded part of the lung (34) via the pleura (39).

The thoracic cavity is not opened in this kind of application and the pleura (39) will not be injured so that a drainage situation is avoided following treatment and bacteria cannot enter the thorax.

For reasons of space, the ultrasonic transducer (49) preferably consists of combined diagnostic-therapeutic elements. As the ultrasonic transducer (49) can only change its position with respect to the depth in a very limited way, the depth of the therapeutic area (46) is preferably controlled by beam forming and the elements of the sound transducer are electronically actuated according to phase shifting.

The therapeutic area (46) of the ultrasonic transducer (40) can reach all areas of the lung tumor (35) by tilting and rotation movements and/or electronic focusing (beam forming). It is recommended that the ultrasonic transducer (40) should have a tilted design so as to be able to reach the areas below the ribs (38) by rotating the grip (48).

This application is optimal for the minimally invasive therapy of a lung tumor (35) which is surrounded by flooded lung tissue (34). In this position below the region of the ribs (38), obstructive structures such as ribs (38) or connective muscle tissue (37) do not exist.

Thus, regardless of the anatomy of the ribs (38) and the location of the lung tumor (35), access can be provided. If multiple foci or foci which are hard to be reached extracostally are to be treated in the upper lung segments, an ideally positioned transducer access can be provided without opening the thorax.

FIG. 4 shows the schematic function sequence and the apparatus for controlling an ultrasound therapy area for the extracostal application of the ultrasonic transducer (40) within the end points (60 and 61) of the angular range (6) for the ablation of lung tumors (35) which are surrounded by flooded lung tissue (34).

The procedure described here refers to the application according to FIG. 3a and illustrates the approach and control of the therapeutic ultrasound transducer (40) to be able to treat a lung tumor (35) surrounded by flooded lung tissue (34) under the anatomical conditions given.

In FIG. 4, a flooded lung (34) with at least one lung tumor (35) is shown. At least one therapeutic ultrasonic transducer (40) is positioned outside the body and acoustically coupled to the thorax.

The ultrasonic transducer (40) has rotatory and translational degrees of freedom (arrows) to be realized via electronic or mechanical methods.

The therapeutic effective area (46) of the ultrasonic transducer (40) is orientated towards the tumor volume. The sound energy is guided between two ribs (38) into the flooded lung (34) via the muscles of the intercostal space (37).

Since the volume of the lung tumor (35) is generally many times greater than the therapy volume (46), the ultrasonic transducer (40) must change its location or characteristics that determine the focal position in order to be able to reach all areas of the volume of the lung tumor (35).

For clarification in the schematic representation, the ultrasonic transducer (40) is simply assumed to be focusing and the transducer surface assumes that the position and size of the therapeutic area (46) are constant.

Due to the high absorption of the ultrasonic energy in the ribs (38) it must be ensured that the ultrasonic energy which is emitted by the ultrasonic transducer (40) and accumulates in the therapeutic area (46) does not impact the ribs (38). This would cause localized heating, which could lead to damage in this area.

According to the invention, this condition is achieved by placing the swivel axis of the ultrasonic transducer (40) into the center (53) between two adjacent ribs (38).

A rotation of the ultrasonic transducer (40) around this virtual axis makes it possible to swivel the therapeutic area by an angular range (6). In this way, the rotation of the ultrasonic transducer (40) around this virtual axis and its translation, i.e. length of a leg, makes it possible to place the effective area in the entire lung tumor (35) without exposing the ribs (38) to ultrasound energy.

There are a number of options which selectively deactivate elements of a large ultrasonic transducer (40), which covers the area of several ribs (38), and thus minimize the exposure of the ribs to ultrasound. This can also be applied to lung tumors (35) surrounded by flooded lung tissue (34), whereby this simple construction with a focusing ultrasound transducer (40) guided by suitable algorithms allows a cost-effective procedure without causing damage to the ribs (38).

FIG. 5 represents the flooded lung (34) with a central lung tumor (35) with the therapy area of a movably arranged therapeutic ultrasound transducer (40) being directed on it.

The kind of application can be freely chosen (see FIG. 3a-d), provided that all spatial points of the tumor P1 to Pn+1 can be accessed through the change in position and/or the beam forming of the therapeutic area (46) of the ultrasonic transducer (40).

The imaging-monitoring system (42) is preferably an ultrasound or MRT system.

The image data are used to assign the information for the temperature-monitoring system (41) in the tumor volume. These data, which contain the tumor localization and spatial temperature information, are transferred to the control unit (5).

Basically, two principles exist for controlling the therapeutic area in the tumor volume; however, combined forms are also possible:

First, the sequential ablation: In this method, the tumor volume is scanned in the position of P1 . . . Pn+1 and this is done in each position of the effective area until the temperature in the therapy volume reaches a necrotic dose of T>55° C.

In this way, all tumor cells in this position (Pn) of the therapeutic area (46) are destroyed.

If the volume of the lung tumor (35) is sequentially scanned from the spatial points P1 to Pn+1, the therapy of the lung tumor (35) is completed after reaching the last position Pn+1.

The advantage of this method is the simple control sequence (almost no closed loop elements).

The disadvantage of this approach, however, is the high susceptibility to motion artifacts, as areas come out of focus and cannot be completely treated. Moreover, the scanning of large tumor volumes is very time-consuming.

As an alternative to the first variant described above, the spatial points P1 to Pn+1 can be scanned again in a controlled adjustment of the position of the therapeutic areas. Here, the therapeutic area remains in a spatial point (Pn) for a relatively short time compared to the sequential method and is thus heated only by a small energy input (e.g. <5° C.).

This single dose is not sufficiently lethal. Due to the continuous, repetitive scanning of the positions (P1 to Pn+1) on at least one therapy loop (70) over a certain period, the entire tumor volume is heated up more or less equally. The temperature in the tumor volume increases relatively constantly until a predetermined temperature distribution or a temperature of >55° C. is reached throughout the lung tumor (35).

The advantage of this method is that motion artifacts and inhomogeneities in absorption capacity are compensated because the thermal energy is propagated in the tumor volume by convection. The total time of therapy decreases significantly in case of larger tumors.

The disadvantage of this approach, however, is that the control and monitoring efforts are increased so that a high-performance mechanical-electrical control (44; 45) of the sound transducer (40) and an iterative algorithm (55) capable of processing large data volumes are required.

This algorithm can also include a combination of these two principles.

The iterative method is beneficial at the location of the lung tumor in the flooded part of the lung (34), since motion artifacts caused by heartbeat and breathing movement can be expected here. Based on a default setting of the positions of the effective area of the transducer (46) in the tumor volume, the therapeutic area is scanned along the spatial points P1 to Pn+1 such that the transducer passes all spatial points (P1 to Pn+1) in one loop (70) within a time period, for example within one second. In parallel, the imaging system records the real temperature distribution, for example within this one second.

In the algorithm, the measured temperature distribution (D1) is compared with one punctual or 2- to 3-dimensional final temperature distribution (D2) predefined by the user or system.

On the basis of the difference between the two data, the location of the spatial points (Pn . . . Pn+1) and optionally the performance in the specific spatial point are adjusted and thus the spatial distribution of the energy input is changed.

In order to achieve homogeneity of the temperature distribution, the temperature distribution measured is compared with a temperature distribution expected at this time. On the basis of this comparison, spatial areas are found which are above or below this value.

In the areas with higher temperature distribution, the performance of the ultrasound transducer is reduced when passing this area, whereas it is decreased when passing areas with lower temperature distribution.

The process (A2) in the algorithm (55) converts this information into a data set, which contains new performance and position data, and delivers this new data set to the control unit (44) and the motor unit (45) of the ultrasonic transducer (40). Thus, the measured, real temperature distribution is iteratively adjusted to the default target distribution. If this target distribution is reached, which is the case at >55° C., or if a sufficient necrotic dose has been administered in each tumor volume, the therapy will be terminated.

FIG. 6 shows the course of the pressure-time diagram of the flooding at different points in time (T):

(Period T0 to T1)

Figure 1A:
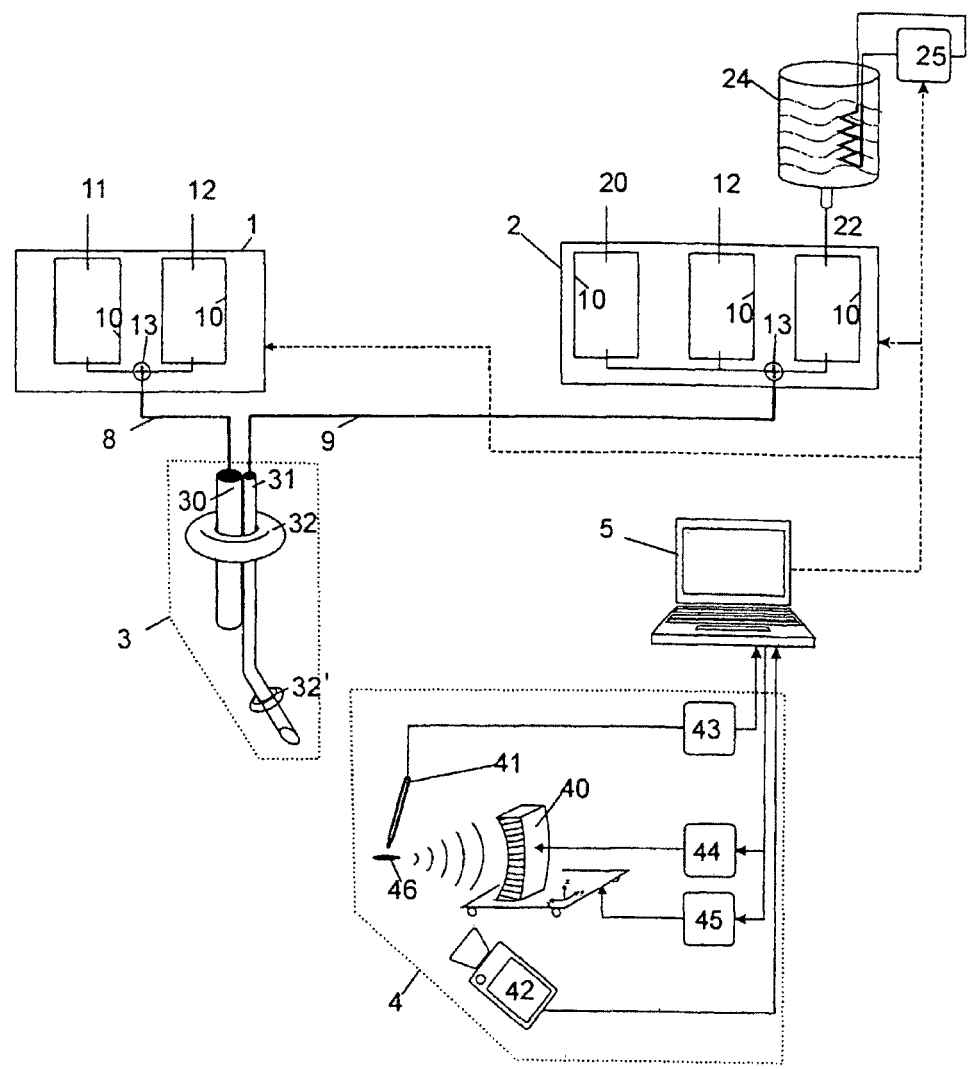
Figure 1B:
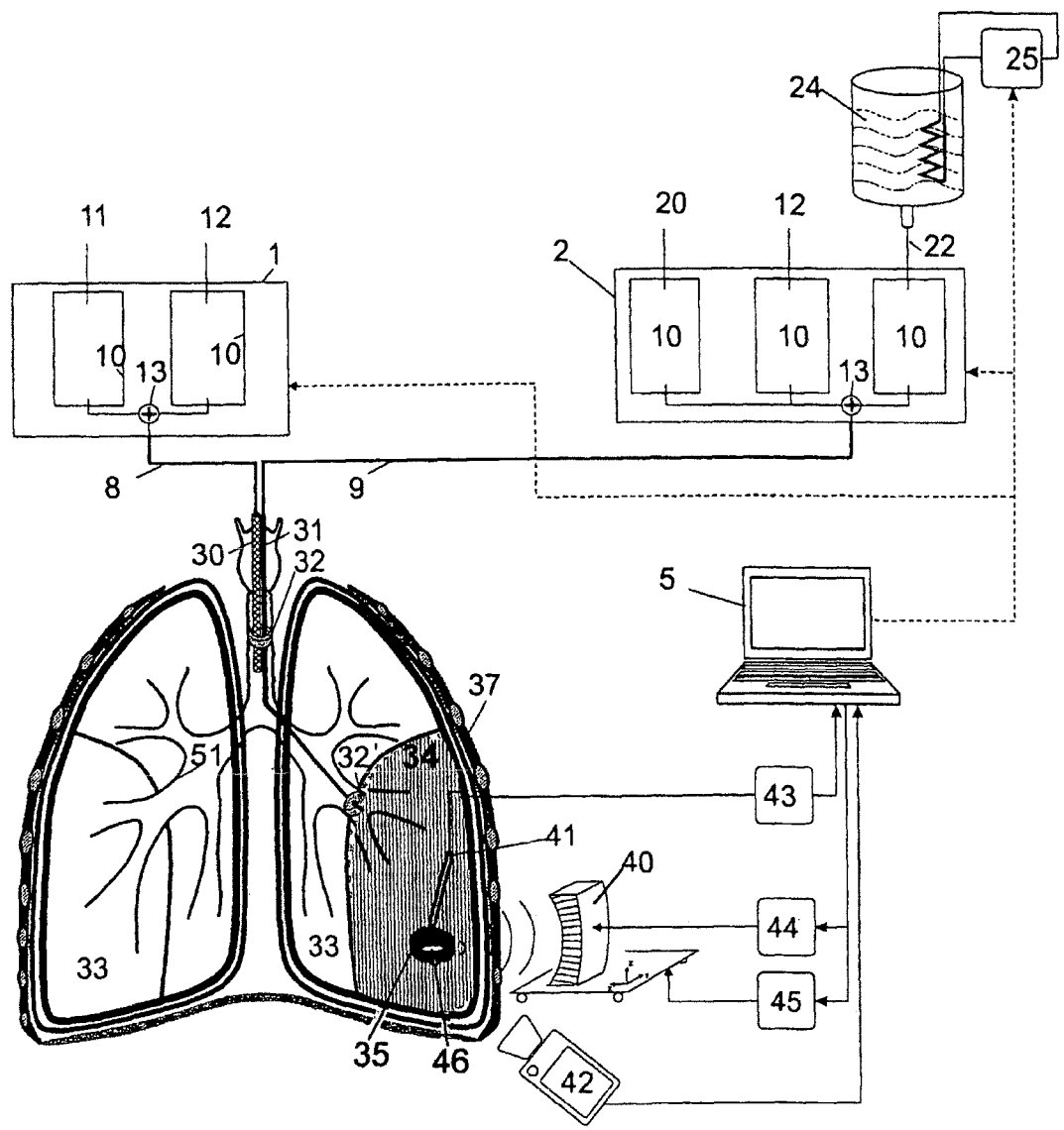
Figure 2:
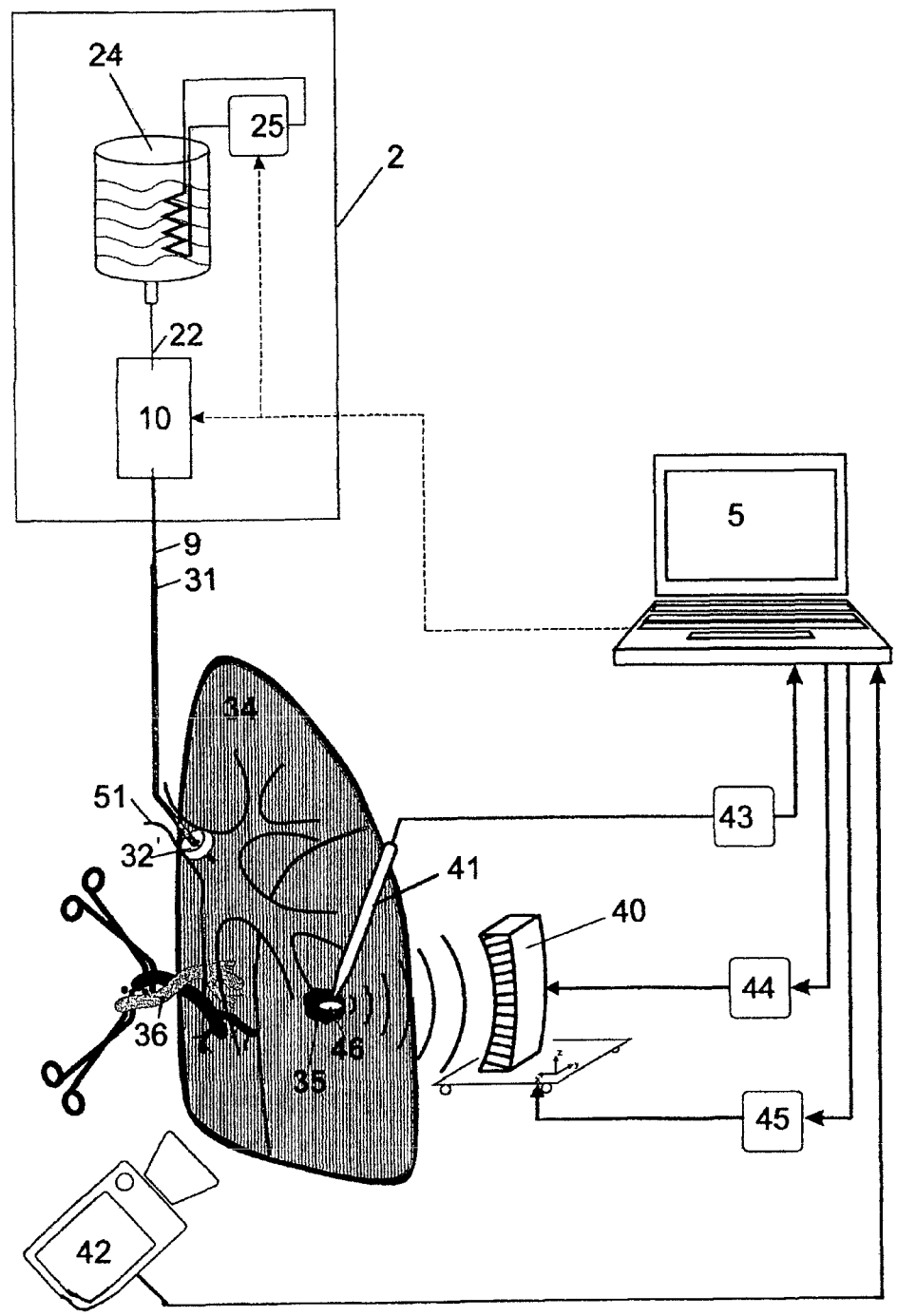
Figure 3A:
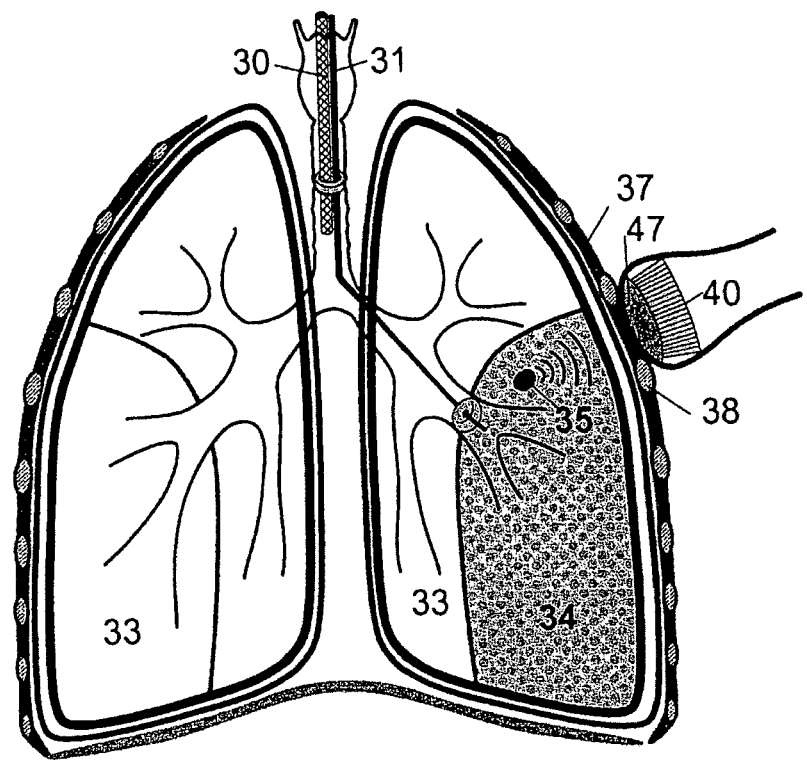
Figure 3B:
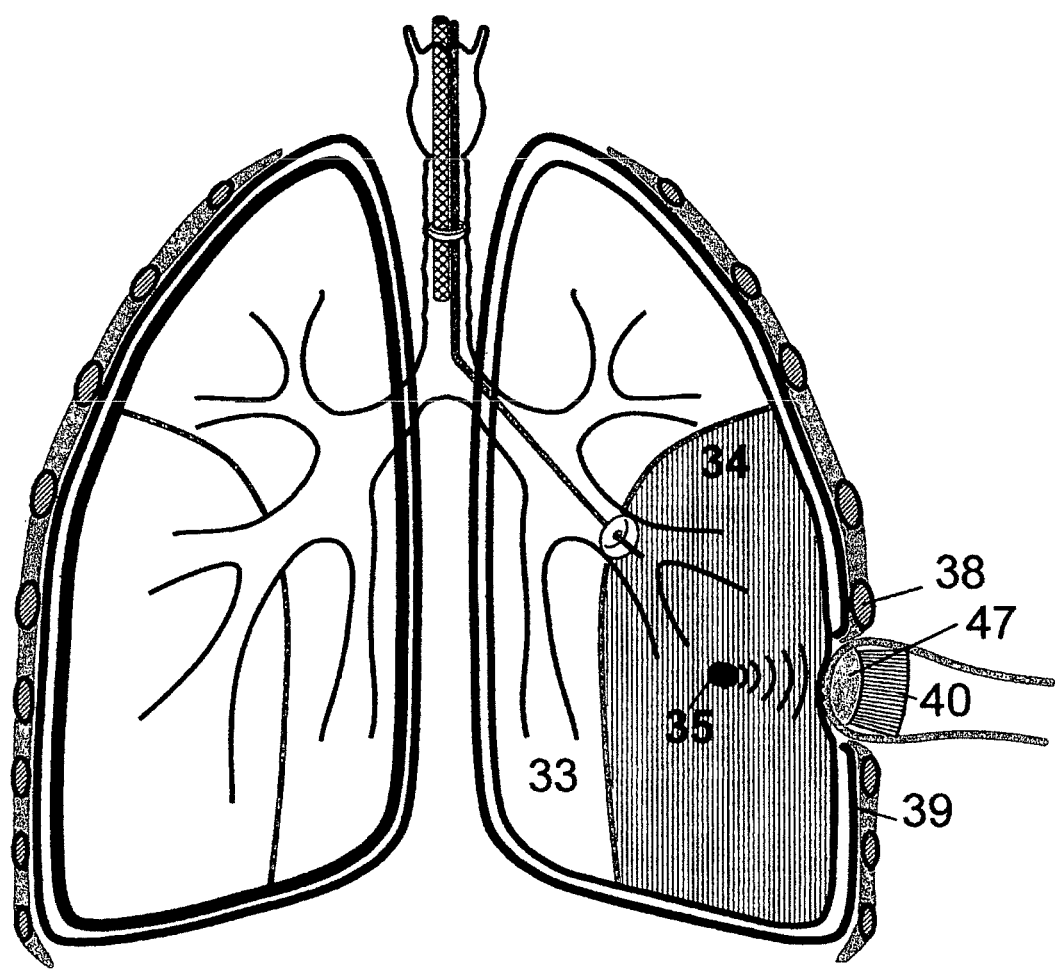
Figure 3C:
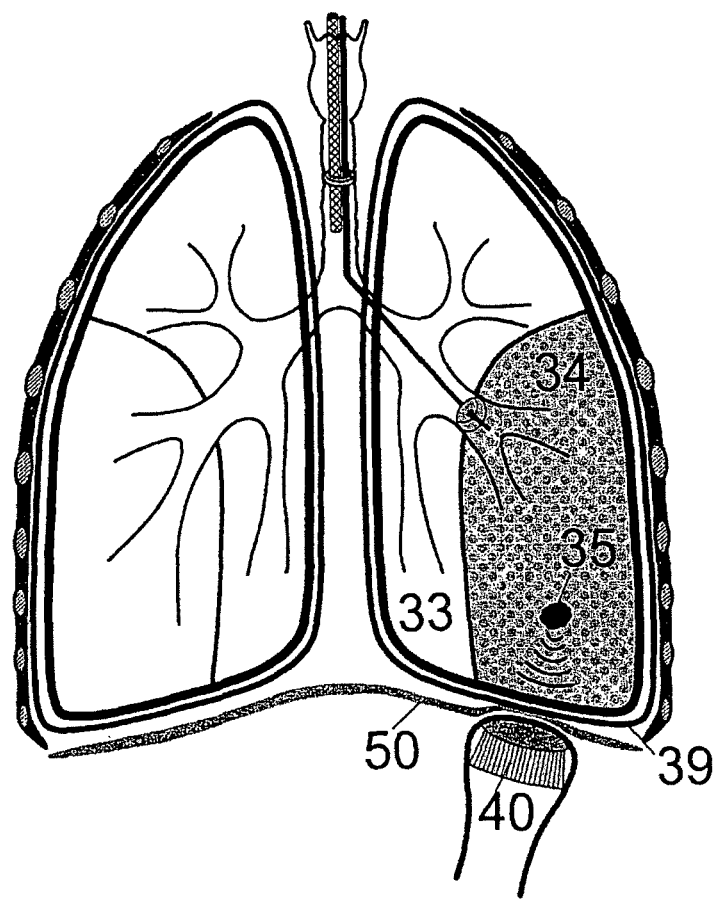
Figure 3D:
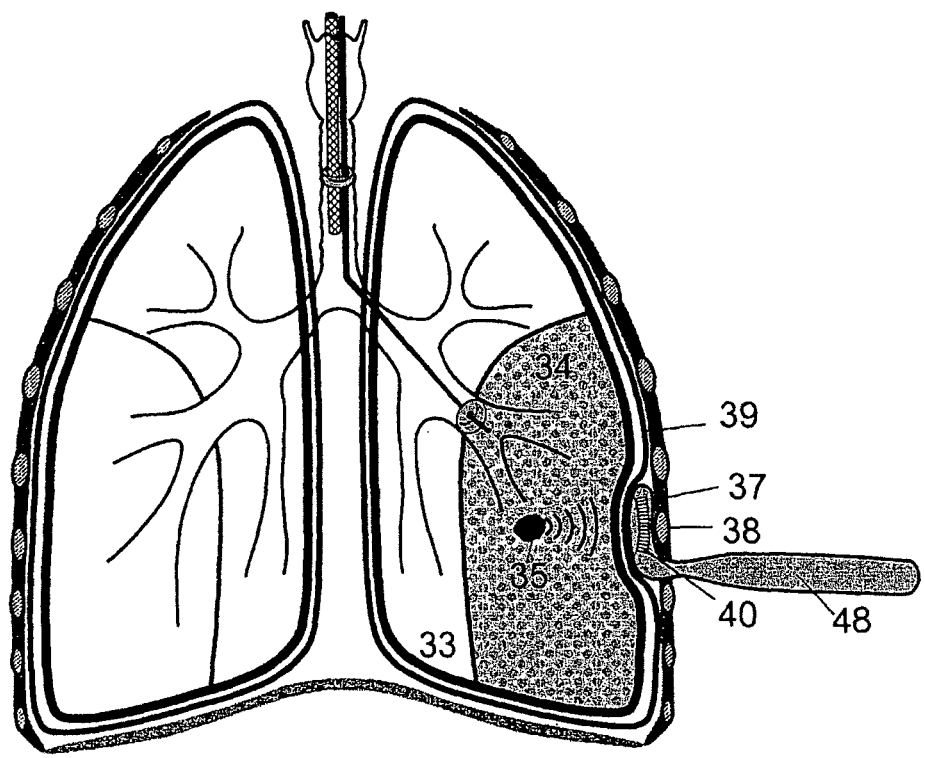
Figure 4:
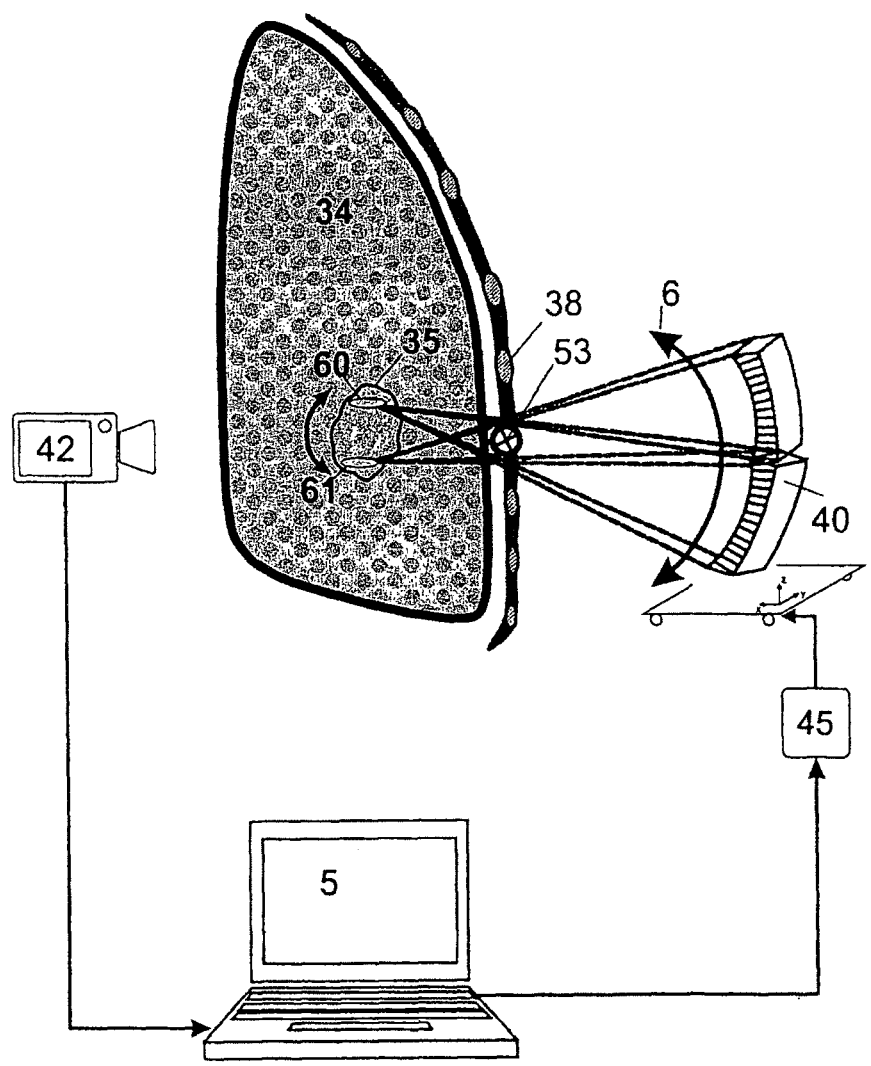
Figure 5:
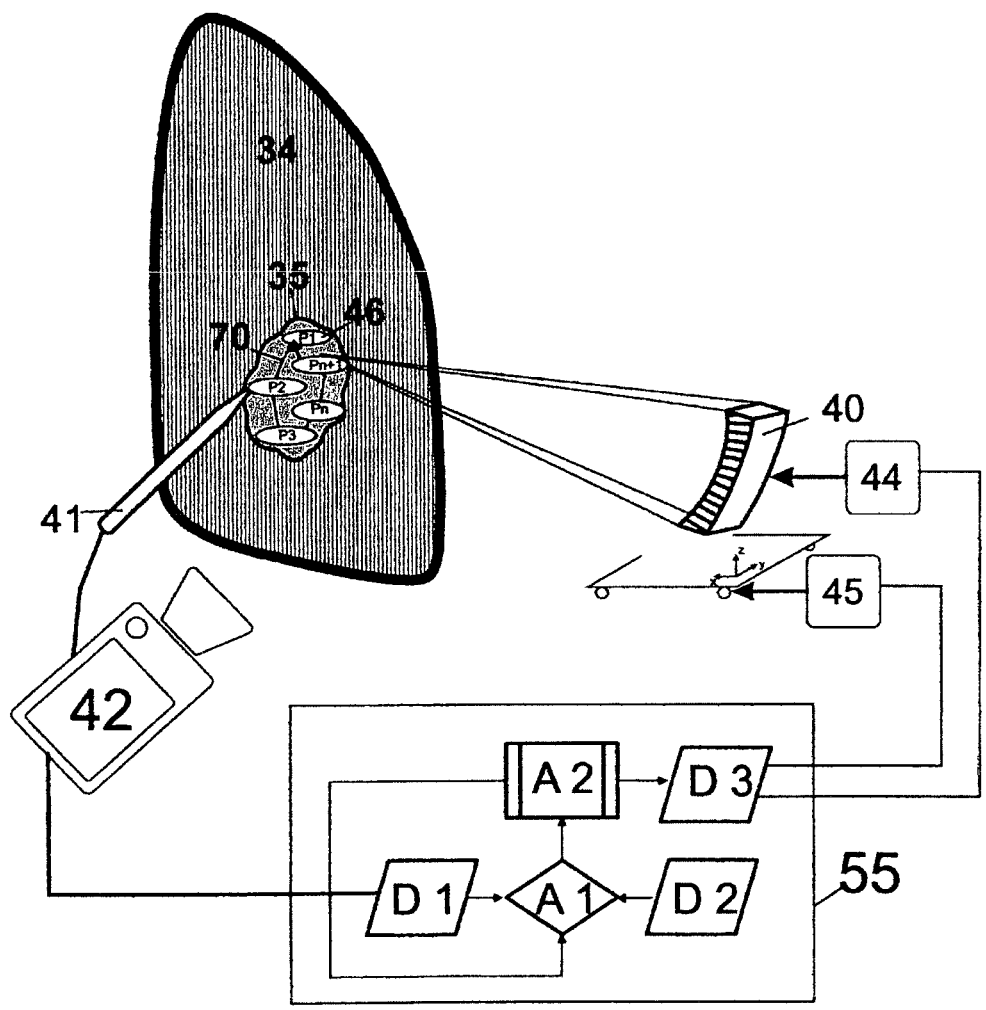
Figure 6:
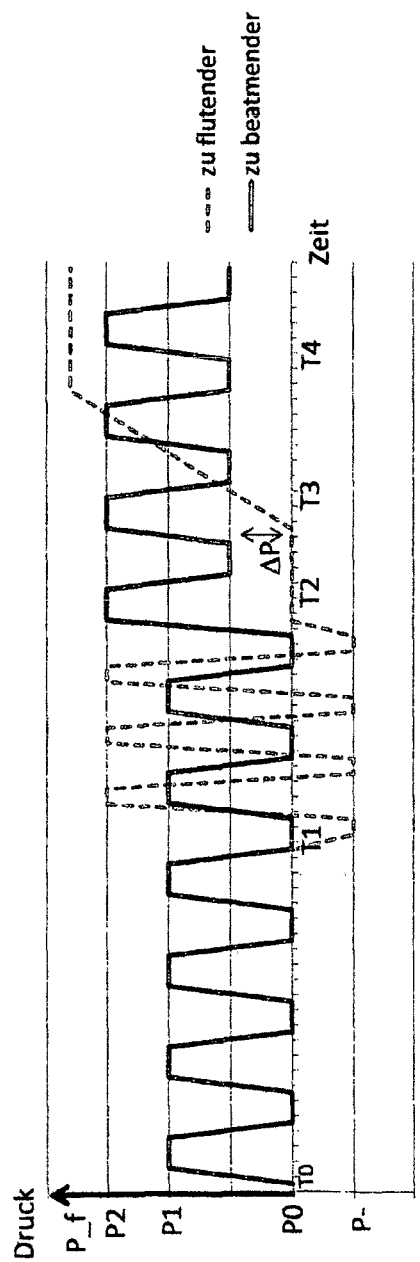
FIGS. 6 and 7 represent a schematic view of the flooding with respect to the pressure and ventilation characteristics.

Before flooding, pure oxygen ventilation takes place by controlling an expiratory (P to P0) and an inspiratory (P1 to P2) pressure in the two parts of the lung (ventilated area and area to be flooded). This process is simplified by a respirator system, which is connected to both tubes (30; 31) or which ventilates the entire lung through one tube.

(Period T1 to T2)

The ventilation can also be carried out separately for the two lung areas thus advantageously reducing the duration of the process up to the initiation of flooding. In this approach, the part of the lung to be flooded can be subject to a higher respiratory rate and/or a higher inspiratory, and/or more negative expiratory pressure. This accelerates the oxygen diffusion process, but is not mandatory.

(Period T2 to T3 to T4)

The part of the lung to be flooded (34) is separated from ventilation by switching over the valve (13) in the flooding system (2) and it is connected to the setting device (10) of the liquid to be supplied (24). Preferably, the expiratory and/or inspiratory pressure are/is increased in the ventilated part of the lung, with ΔP corresponding to a pressure difference of approximately 5 to 10 cm $H_2O$. The inflowing liquid distributes itself in the part of the lung to be flooded (34) and presses oxygen in the pulmonary bloodstream. With increasing flooding, the flooding pressure starts to increase from a point in time (T3) because the elasticity of the lung counteracts this flooding. When a predetermined flooding pressure P_f is reached, the flooding process is completed (T4). A successful flooding free of residual gas has been achieved when no echoes of gas bubbles are shown in the ultrasound image of the imaging-monitoring system (42) and the flooded lung tissue with its anatomical structures and the lung tumor (35) become visible. The therapy can now be started.

Figure 7:
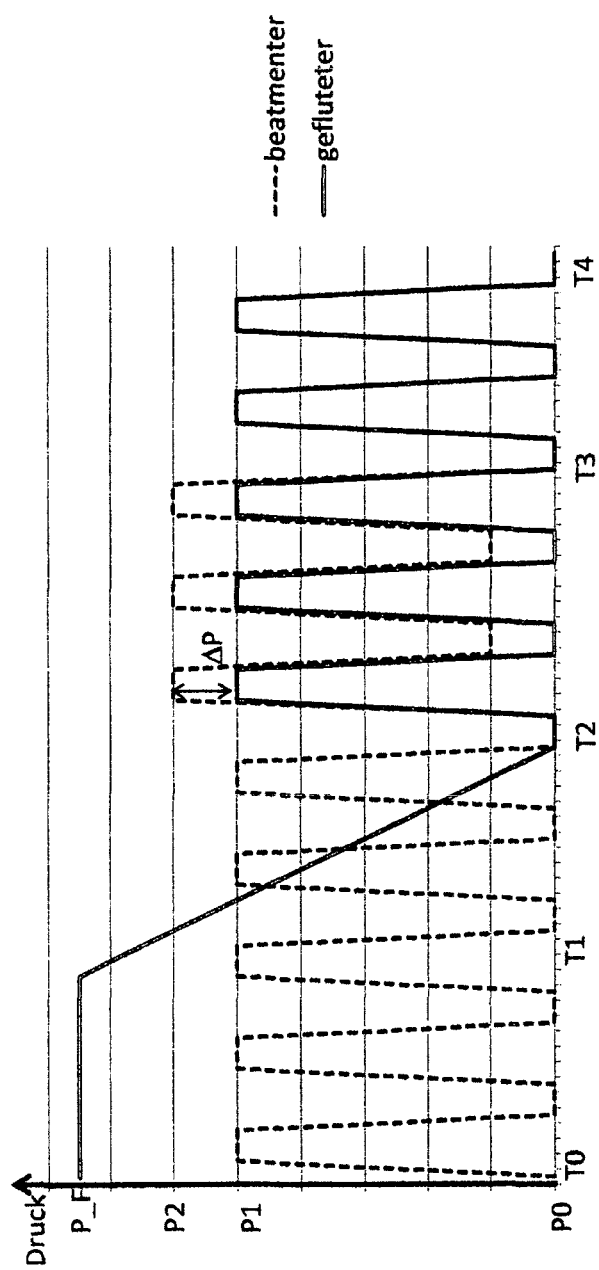

FIG. 7 shows the course of the pressure-time-diagram of deflooding with different points in time (T):

(Period T0 to T1)

The flooding is still complete; the flooding pressure is maintained by the system (2) by means of the setting device (10). The ventilated part of the lung is respirated by a predetermined inspiratory (P1 to P2) and expiratory (P0) pressure, for which pure oxygen or atmospheric gases can be used.

(Period T1 to T2)

The flooding pressure is reduced until it approximately reaches the atmospheric ambient pressure. This is done by controlling the liquid pressure in the device (10) or by switching the control element (13) to the control element of the underpressure supply (20) of the flooding system or by simply disconnecting the supply line (9) to the flooded part of the lung.

(Period T2 to T3)

The flooded part of the lung (34) is connected to the respirator system, and thus air or oxygen is led in. This is done by switching over the control element (13) in order to connect the supply line (9) to a gas-supplying (11 or 12) setting device (10). The example shows a controlled pressurization so that in the non-flooded, respirated part of the lung a pressure is applied which is by approximately 5-10 cm $H_2O$ higher than the pressure in the flooded part of the lung. This condition is kept for a specific period. This optional re-ventilation scheme improves the absorption of the liquid from the flooded part of the lung (34) by the pulmonary bloodstream. In addition, it shortens the process time until the patient can be released from respiration.

(Period T3 to T4)

The flooded and respirated parts of the lung (34 and 33) are commonly supplied with oxygen or atmospheric gas by means of a respirator system until the resorption process of the liquid is completed. This step provides a simplified and practical solution, since the connection of the two tubes (30; 31) or the ventilation via one tube requires only one respirator system (1).

The advantages of the apparatus and method for operating this apparatus for the in-vitro and in-vivo treatment of lung tumors are that the tumor tissue is heated completely and exclusively by the thermal effect of ultrasound and that it is destroyed exclusively by the acoustic-thermal effect of ultrasound. A specific and precisely positioned thermal heating of the tumor tissue is reached in-vitro and in-vivo at a target temperature of >55° C. in the lung tumor.

All features disclosed in the description, the embodiments and the subsequent claims may be essential to the invention both individually and in any combination.

The invention claimed is:

1. A method for in-vitro and in-vivo treatment of a lung tumor by using an apparatus comprising:
    a ventilation and respirator system configured to provide at least a part of the lung containing a tumor with a gas for respiration purposes, the gas including oxygen;
    a system configured for the controlled ventilation and flooding with a liquid said part of the lung;
    a therapy system comprising;
    at least one therapeutic focusable ultrasound transducer on a mount provided with a motor and configured for aiming an ultrasound beam generated by the at least one therapeutic focusable ultrasound transducer, and a beam-forming unit configured to focus the ultrasound beam;
    an imaging-monitoring system configured to generate tumor localization data to locate location points of tissue of a lung tumor spatial point by spatial point; and a temperature-monitoring system configured to measure temperature of the lung tumor tissue and to generate tumor tissue temperature data indicating a distribution of the temperature of the tumor tissue;

a central control unit having data-transferring connections to the motor, the beam-forming unit, the ventilation and respirator system, the system configured for controlled ventilation and flooding, the imaging-monitoring system, and the temperature-monitoring system, wherein the ventilation and respirator system and the system configured for controlled ventilation and flooding have respective gas- and liquid-conducting tubes which comprise respective lumens of a lung tube, the lung tube is configured to be inserted into a lung containing a lung tumor in an intratracheal manner, and the central control unit is configured to compare the measured temperature distribution of the tumor tissue with a predetermined target temperature distribution of the tumor tissue and control the focus, the all1iog and performance of the ultrasound beam generated by the at least one therapeutic focusable ultrasound transducer based on the tumor tissue localization data, the tumor tissue temperature data transferred through the data-transferring connection to the at least one therapeutic focusable ultrasound transducer and the predetermined target tissue temperature distribution, and so that the at least one therapeutic focusable ultrasound transducer scans the location points of the tumor, heats the tumor tissue to a temperature greater than 55° C. by the thermal effect of the focused ultrasound beam, and destroys the tumor tissue by acoustic-thermal effects of the focused ultrasound beam, and wherein the central control unit is configured so that in areas scanned by at least one therapeutic focusable ultrasound transducer in which the measured distribution of temperatures of the tumor tissue is below or above the target distribution performance of the at least one therapeutic ultrasound transducer is increased or decreased, respectively, and the measured temperature distribution of the tumor tissue is iteratively adjusted to the target temperature distribution of the tumor tissue;

the method comprising:

arranging the lung tube so that the lung tube communicates with a lung containing a tumor and isolating the lumens of the lung tube from each other with respect to liquid and gas, the tumor having tumor tissue defining a tumor volume comprising spatial points of the tumor;

saturating, through one of the lumens of the lung tube connected to the ventilation and respirator system, at least a part of the lung containing the tumor by ventilation with oxygen or air;

flooding, through the other one of the lumens of the lung tube, the part of the lung containing the tumor with liquid to provide a flooded part of the lung while controlling pressure and volume of the liquid, the liquid being physiologically compatible and essentially acoustically identical to lung tissue of the lung and continuing the ventilation with a non-flooded part of the lung;

terminating, during the flooding, the ventilation with oxygen and increasing pressure of the liquid in the lung containing the tumor;

terminating the flooding with liquid when a threshold of pressure or volume of the liquid is reached;

effecting targeted, controlled emission of therapeutic doses of focused ultrasonic energy through the lung tissue of the lung and the liquid in the flooded part of the lung into the tumor tissue, spatial point by spatial point of the tumor volume, thereby to heat the tumor tissue by the thermal effect of the focused ultrasonic energy to a temperature greater than 55° C. and destroy the tumor tissue by acoustic-thermal effects of the focused ultrasonic energy; and reconnecting the flooded part of the lung to ventilation, during which the liquid, which remains in the lung, is resorbed into a body of a person whose lung is the subject of the lung tumor treatment.

2. The method for in-vitro and in-vivo treatment of a lung tumor according to claim 1, wherein the control unit has an information-transmitting connection to at least one control element by means of which gas- and liquid flows can be introduced in a controlled manner into the lung tube via at least one supply line.

3. The method for in-vitro and in-vivo treatment of a lung tumor according to claim 1, wherein at least one of the tubes which comprise the lung tube is provided with a block configured to form a gas- and liquid-tight seal in bronchi or lower trachea of the lung.

4. The method for in-vitro and in-vivo treatment of a lung tumor according to claim 1, wherein the central control unit is configured to control and regulate pressures and volume flows of the gas and the liquid.

5. The method according to claim 1, wherein the thermal effect of the focused ultrasonic energy exclusively heats the tumor tissue.

6. The method according to claim 1, wherein the acoustic-thermal effect of the focused ultrasonic energy exclusively destroys the tumor tissue.

* * * * *